United States Patent [19]
Volkov et al.

[11] 3,993,055
[45] Nov. 23, 1976

[54] APPARATUS FOR SURGICAL TREATMENT OF BONE FRACTURES AND DISEASES

[76] Inventors: Mstislav Vasilievich Volkov, 1 Stroitelnaya ulitsa, 6, korpus 1, kv. 63; Oganes Vardanovich Oganesian, ulitsa Pervomaiskaya, 74, kv. 87, both of Moscow, U.S.S.R.

[22] Filed: June 11, 1975

[21] Appl. No.: 586,136

[52] U.S. Cl. .............................. 128/84 B; 128/92 A
[51] Int. Cl.² ........................................... A61F 5/04
[58] Field of Search .............. 128/84 R, 84 B, 84 C, 128/83, 87, 92 R, 92 A, 92 B, 92 E

[56] References Cited
UNITED STATES PATENTS

| | | | |
|---|---|---|---|
| 2,120,446 | 6/1938 | Thomas | 128/84 B |
| 2,406,987 | 9/1946 | Anderson | 128/92 A |
| 2,687,720 | 8/1954 | Haboush | 128/84 R |
| 3,727,610 | 4/1973 | Riniker | 128/92 A |

*Primary Examiner*—John D. Yasko
*Attorney, Agent, or Firm*—Steinberg & Blake

[57] ABSTRACT

The proposed apparatus for surgical treatment of bone fractures and diseases comprises two pairs of needles each of which is to be driven through one of the bone fragments being aligned. Each pair of needles is secured in at least one brace so that each pair of needles and the brace define a rigid system to be secured on the respective bone fragment. The two rigid systems are interconnected by distractors. Accordingly, the end of the distractors are fastened to sliders moving in mutually perpendicular guide slots formed in the opposite braces belonging to different rigid systems.

The apparatus of the invention permits repositioning bone fragments and effecting compression thereof both lengthwise in transverse fractures and laterally in oblique and spiral fractures.

4 Claims, 3 Drawing Figures

APPARATUS FOR SURGICAL TREATMENT OF BONE FRACTURES AND DISEASES

The present invention relates to medical technology, and, more particularly, to apparatus for surgical treatment of bone fractures and diseases.

The proposed apparatus may find application in orthopaedics and traumatology for repositioning bone fragments in fractures followed by their secure fixation in the compression position, for lengthening shortened bones and for compression arthrodesis.

It is widely known in the art to employ apparatus for surgical treatment of bone fractures and diseases (see, for instance, U.S.S.R. Inventor's Certificate No. 247,454) which comprise at least two pairs of needles. The tips of the needles of each pair are secured in one brace or in two rigidly interconnected braces so that each pair of needles and the brace(s) define a rigid system. The needles of each rigid system are driven through one of the bone fragments being aligned. Said rigid systems are interconnected by means of distractors which are rigidly coupled to both rigid systems. The distractors are formed as split members held together by split nuts which enable the distance between the braces interconnected by the distractors to be varied. The two rigid systems are further interconnected by a screw coupling disposed at an angle to the longitudinal axis of the apparatus and serving to effect lateral compression of the bone fragments.

Application of the apparatus starts by driving the needles through the bones being aligned. After a pair of needles has been driven through each bone fragment at points corresponding to the positions of the needles in the apparatus, the needles are tensioned and fixed in the respective braces.

After the apparatus has been applied, the repositioning procedure is initiated. To correct a lengthwise displacement of the bones, the split nuts of the distractors are manipulated; to correct lateral displacements of the bones, the nut of the screw coupling is turned.

However, the prior art apparatus cannot completely reposition the bone fragments being aligned as it fails to correct their lateral displacements in the frontal and sagittal planes of the body.

It is an object of the present invention to provide an apparatus for surgical treatment of bone fractures and diseases of such a design as would enable bone fragments to be accurately and proportionately repositioned in all planes and securely fixed subsequently for the entire period of time required to effect a bony union.

The foregoing object is attained in an apparatus for surgical treatment of bone fractures and diseases, comprising at least two pairs of needles to be driven through the bones being aligned, the tips of the needles of each pair secured in at least one brace so that each pair of needles and the brace define a rigid system to be secured on the respective bone being aligned, and also comprising distractors serving to interconnect said rigid systems as well as to vary the distance therebetween, wherein, in accordance with the invention, in the ends of the opposite braces belonging to different rigid systems there are formed mutually perpendicular guide slots lying in the planes of the braces, said guide slots accommodating sliders provided with actuators for moving the sliders in the guide slots and locking them in a desired position, and the distractors are coupled at the opposite ends thereof with said sliders.

The distractors coupled with the sliders may be provided with universal joints installed in the midportion of each distractor.

The midportions of the opposite braces belonging to different rigid systems may be interconnected by a distractor provided with a universal joint in the midportion thereof.

The proposed apparatus has a wider functional scope than the prior art one. It permits accurate repositioning of bone fragments in recent and inveterate fractures and their subsequent locking in the compression or distraction positions. Used for lengthening an extremity, the apparatus of this invention enables the bone fragments to be kept in precise alignment for the whole duration of the lengthening process.

The proposed apparatus enables compression of the bone fragments to be achieved not only lengthwise in lateral fractures, but also in a transverse direction in oblique and spiral fractures.

The invention will be further understood from the following description of an exemplary embodiment thereof taken in conjunction with the accompanying drawings, wherein.

Figure 1:
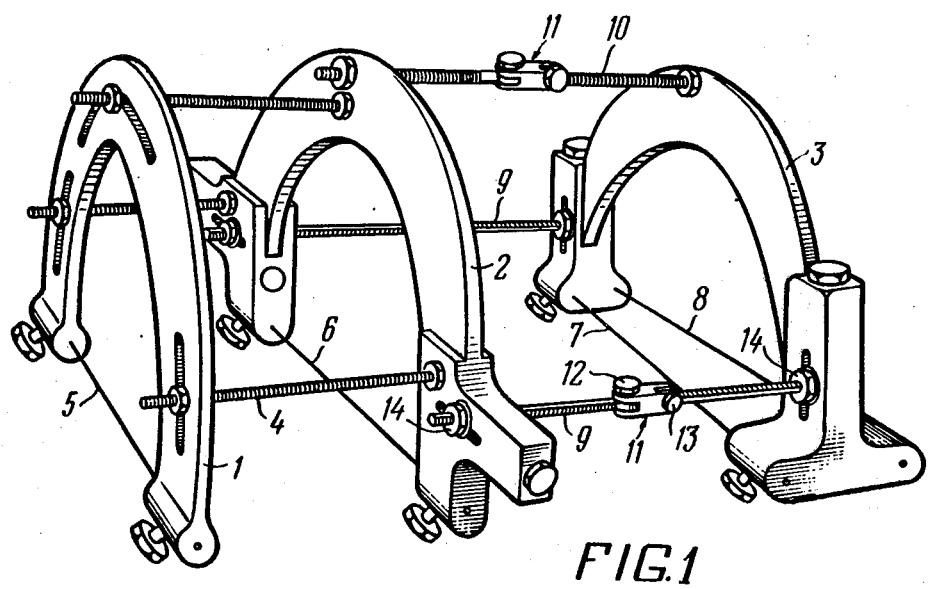
FIG. 1 is a general schematic view of an apparatus for surgical treatment of bone fractures and diseases, in accordance with the invention.

Referring now to the drawings, the proposed apparatus for surgical treatment of fractures and diseases of joints comprises three braces 1, 2 and 3 (FIG. 1). The braces 1 and 2 are interconnected by three tie bolts 4. Needles 5 and 6 are respectively secured in the braces 1 and 2, whereas needles 7 and 8 are both secured in the brace 3. The needles 5 and 6 together with the braces 1 and 2 define a rigid system to be secured on one bone fragment, while the needles 7 and 8 together with the brace 3 define a second rigid system to be secured on the other bone fragment aligned with the former one. The two rigid systems are interconnected by distractors 9. The midportions of the braces 2 and 1 may likewise be interconnected by a distractor 10. In the midportion of each distractor 9 and 10 there is provided a universal joint 11 comprising two uniaxial links 12 and 13 with mutually perpendicular axes. To vary the distance between the braces 2 and 3, and hence between the bone fragments fixed in the apparatus, the distractors 9 and 10 are provided with a screw thread and fastened to the braces 2 and 3 with the aid of split nuts 14.

There are two guide slots 15 (FIG. 2) formed in the ends of the brace 3. Each guide slot 15 lies in the plane of the brace 3 and accommodates a slider 16, the distractor 9 coupled with the slider 16 passing through a hole formed in the slider 16. The slider 16 is propelled along the guide slot 15 and locked in position therein by a drive screw 17.

Figure 2:
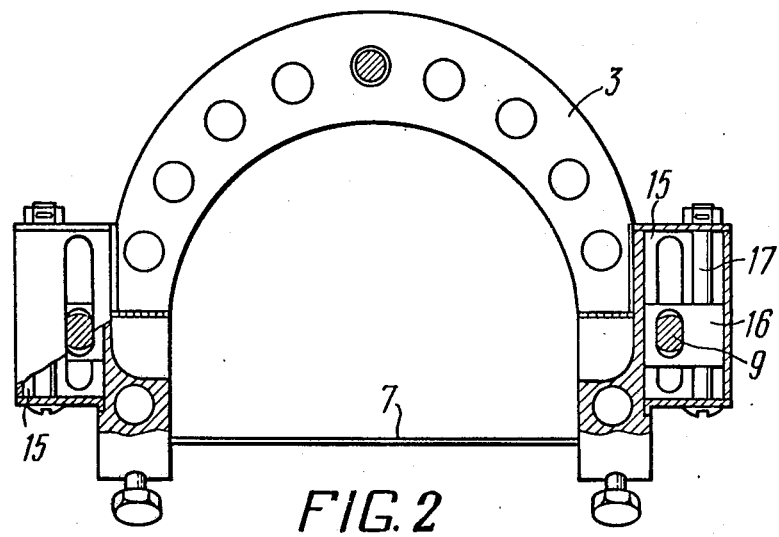
FIG. 2 illustrates one of the braces of the apparatus with the distractors secured therein, shown partially in section, in accordance with the invention.

The brace 2 (FIG. 1) disposed opposite the brace 3 and belonging to a different rigid system has two guide slots 18 (FIG. 3) formed in the ends thereof, said guide slots 18 lying in the plane of the brace 2 and being disposed at right angles to the guide slots 15 (FIG. 2).

A slider 19 moves in each guide slot 18 (FIG. 3), the distractor 9 coupled with the slider 19 passing through a hole formed therein. The slide 19 is driven along the guide slot 18 and locked in position therein by a drive screw 20.

As the sliders 16 (FIG. 2) and 19 (FIG. 3) move in their respective guide slots 15 and 18, the two rigid systems defined by the needles and the braces can be displaced in two mutually perpendicular directions.

The proposed apparatus for surgical treatment of bone fractures and diseases functions as follows.

The needles 5 and 6 (FIG. 1) are driven through one bone fragment, tensioned and fixed in the braces 1 and 2, respectively. The other two needles, 7 and 8, are driven through the second bone fragment, tensioned and fixed in the brace 3.

After the apparatus has been applied and the bone fragments immobilized, a procedure of bone fragment repositioning is initiated. To correct a lengthwise displacement of the bone fragments, the split nuts 14 of all distractors 9 and 10 are manipulated. If the lengthwise displacement of the bone fragments is compounded by an angular displacement thereof in the frontal plane of the body, the nut 14 of the distractor 9 on the acute angle side is given a longer travel. In the course of correction of the angular displacement of the bone fragments in the frontal plane, the links 12 of the distractors 9 and 10 are slightly loosened, facilitating the correction procedure. After this kind of displacement has been corrected, said joints 12 are tightened again.

To correct an angular displacement in the sagittal plane of the body, the split nuts 14 of the distractor 10 are manipulated, with the links 13 of the distractors 9 and 10 being slightly loosened for the duration of the correction procedure and retightened after the displacement has been corrected.

Figure 3:
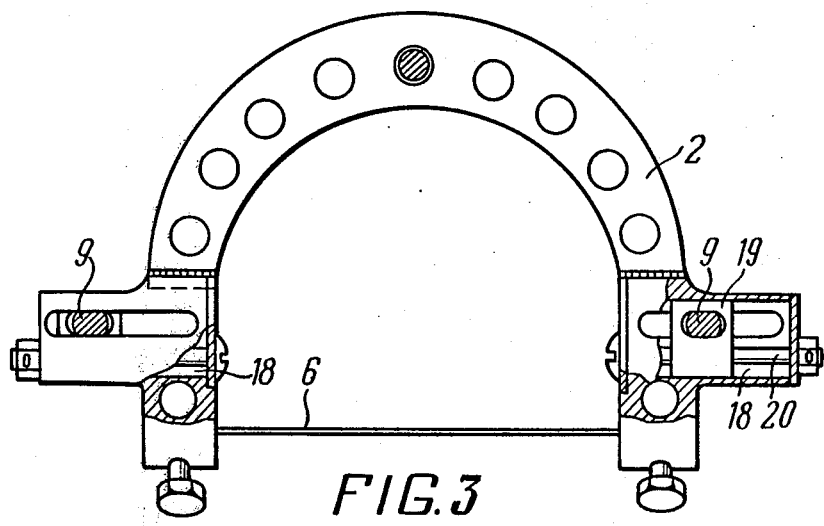
FIG. 3 illustrates another brace of the apparatus with the distractors secured therein, shown partially in section, in accordance with the invention.

A lateral displacement of bone fragments is corrected by moving the sliders 16 (FIG. 2) and 19 (FIG. 3). To correct a lateral displacement of bone fragments in the frontal plane of the body, the drive screw 20 (FIG. 3) is manipulated, while a lateral displacement of bone fragments in the sagittal plane of the body is corrected with the aid of the drive screw 17 (FIG. 2).

Thus, the apparatus of the invention permits effecting a gradual repositioning of the bone fragments followed by fixation thereof in the compression position, bringing about a bony union within a short time.

What is claimed is:

1. An apparatus for surgical treatment of bone fractures and diseases, comprising: two pairs of needles each of which is to be driven through one of the bones to be aligned; at least two braces, the tips of said needles of one of said pairs being secured in each said brace so that the needles and the brace define a rigid system, and one pair of needles with the brace define one rigid system to be secured on one bone being aligned while the other pair of needles and the brace define a second rigid system to be secured on the other bone being aligned; two distractors interconnecting said rigid systems; guide slots formed in the ends of said opposite braces in each of said rigid systems and lying in the plane of said brace, said guide slots formed in one said brace being disposed at right angles relative to said guide slots formed in said opposite brace; sliders accommodated in said guide slots; actuators for moving said sliders along said guide slots and fixing said sliders in a required position; the ends of said distractors being coupled with said sliders.

2. An apparatus as set forth in claim 1, wherein said distractors coupled with said sliders are provided with universal joints disposed approximately in the middle of each said distractor.

3. An apparatus as set forth in claim 1, comprising a distractor which interconnects the midportions of said opposite braces each of said rigid systems.

4. An apparatus as set forth in claim 2, comprising: a distractor interconnecting the midportions of said opposite braces each of said rigid systems; a universal joint disposed approximately in the midportion of said distractor.

* * * * *